(12) United States Patent
Maytom

(10) Patent No.: US 6,436,944 B1
(45) Date of Patent: Aug. 20, 2002

(54) COMBINATION EFFECTIVE FOR THE TREATMENT OF IMPOTENCE

(75) Inventor: Murray C. Maytom, Darien, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/636,407

(22) Filed: Aug. 10, 2000

Related U.S. Application Data

(60) Provisional application No. 60/156,750, filed on Sep. 30, 1999.

(51) Int. Cl.$^7$ .................... A61K 31/495; A61K 31/195; A61K 31/440
(52) U.S. Cl. ........................ 514/258; 514/275; 514/312; 514/349; 514/353; 514/355
(58) Field of Search ................................ 514/258, 275, 514/312, 349, 353

(56) References Cited

U.S. PATENT DOCUMENTS

| | | | |
|---|---|---|---|
| 5,336,678 A | * 8/1994 | Cavallini | 514/275 |
| 5,488,059 A | * 1/1996 | Buhl | 514/349 |
| 5,899,875 A | * 5/1999 | Millot et al. | 604/20 |
| 6,037,346 A | * 3/2000 | Doherty et al. | 514/258 |
| 6,124,461 A | * 9/2000 | Shoemaker | 546/147 |
| 6,184,231 B1 | * 2/2001 | Hewawasam et al. | 514/312 |
| 6,214,849 B1 | * 4/2001 | Saxena et al. | |
| 6,266,560 B1 | * 7/2001 | Zhans et al. | 604/20 |
| 6,277,884 B1 | * 8/2001 | de Tejada | |
| 6,331,543 B1 | * 12/2001 | Garvey et al. | |

FOREIGN PATENT DOCUMENTS

| WO | 942 8902 | 12/1994 |
|---|---|---|

OTHER PUBLICATIONS

Kanba, et al., J. Neurochem., vol. 57, No. 6, 1991 "Two Possibly Distinct Prostaglandin $E_1$ Receptors in N1E–115 Clone: One Mediating Inositol Trisphosphate Formation, Cyclic GMP Formation, and Intracellular Calcium Mobilization and the Other Mediating Cyclic AMP Formation".

Wei, A., et al., Science (1990) vol. 248 pp. 599–603 "$K^+$Current Diversity Is Produced by an Extended Gene Family Conserved in Drosophila and Mouse".

Lazdunski (1992); M. Lazdunski, et al., "ATP–Sensitive K<+> Channels", Renal Physiol. Biochem. vol. 17: pp. 118–120 (1994) "ATP–Sensitive $K^+$ Channels".

Noma, A. Nature (1983) vol. 305 pp. 147–148 "ATP–regulated $K^+$ channels in cardiac muscle".

Cook, et al, Nature (1984) vol. 311 pp. 271–273 "Intracellular ATP directly blocks $K^+$ channels in pancreatic B–cells".

Nelson, M.T. et al., Am. J. Physiol. (1990) vol. 259 pp. C3–C18 "Calcium channels, potassium channels, and voltage dependence of arterial smooth muscle tone".

Wang, W., et al, Am. J. Physiol. (1990) vol. 258, pp. F244–F253 "A potassium channel in the apical membrane of Rabbit thick ascending limb of Hewlet's loop".

Cook, et al., "Potassium Channels: Structure, Classification, Function and Therapeutic Potential", ed. N.S. Cook, Ellis Horwood, Chichester (1990), pp. 181–255 "Potassium channel pharmacology".

David W. Robertson, et al., Journal of Medicinal Chemistry, "Potassium Channel Modulators: Scientific Applicants and Therapeutic Promise" vol. 33, No. 6, Jun. 1990, pp. 1529–1541 "Potassium Channel Modulators: Scientific Applications and Therapeutic Promise".

Gillian Edwards et al., "Structure–Activity Relationships of K + Channel Openers", vol. 11, No. 10, Oct. 1990, pp. 417–422 "Structure–activity relationships of $K^+$ Channel openers".

Valerie A. Ashwood, et al., "Synthesis and Antihypertensive Activity of Pyran Oxygen and Amide Nitrogen Replacement Analoges of the Potassium Channel Activator Cromakalim", Journal of Medicinal Chemistry, vol. 34, No. 11, Nov. 1991, pp. 3261–3267.

Susan D. Longman, et al., "Potassium Channel Activator Drugs: Mechanism of Action, Pharmacological Properties, and Therapeutic Potential ", Medicinal Research Reviews, vol. 12, No. 2, Mar. 1, 1992, pp. 73–148.

Karnail S. Atwal, "Modulation of Potassium Channels by Organic Molecules", Medicinal Research Reviews, vol. 12, No. 6 Nov. 1992, pp. 569–591.

* cited by examiner

*Primary Examiner*—Shep K. Rose
(74) *Attorney, Agent, or Firm*—Peter C. Richardson; Gregg C. Benson; Arlene K. Musser

(57) ABSTRACT

This invention relates to the treatment of erectile dysfunction with a combination of (1) a compound selected from potassium channel openers, and (2) a compound selected from compounds which elevate cGMP levels. Sildenafil or a pharmaceutically acceptable salt thereof is preferred as the cGMP PDE elevator. Also included are compositions and kits comprising such impotence treating compounds.

25 Claims, No Drawings

COMBINATION EFFECTIVE FOR THE TREATMENT OF IMPOTENCE

This application claims priority from provision application U.S. serial No. 60/156,750 filed Sep. 30, 1999, the benefit of which is hereby claimed under 37 C.F.R.§1.78(a)(3).

FIELD OF THE INVENTION

This invention relates to the treatment of impotence comprising co-administering (1) a potassium channel opener and (2) a compound which elevates cyclic guanosine 3',5'-monophosphate (cGMP) levels. The combination is particularly suitable for the treatment of patients suffering from impotence or erectile dysfunction.

BACKGROUND OF THE INVENTION

Impotence is the inability to obtain and/or sustain an erection sufficient for penetration of the vagina and/or intercourse. Thus, impotence is also referred to as "erectile insufficiency" or "erectile dysfunction". It has been estimated that 10–12 million American men between the ages of 18 and 75 suffer from chronic impotence, with the great majority being over age 55.

The penis normally becomes erect when certain tissues, in particular the corpora cavernosa in the central portion of the penis, become engorged with blood, thereby causing them to become less flaccid, and in turn causing an erection. Impotence can result from psychologic disturbances (psychogenic), from physiologic abnormalities (organic) or from a combination of both. Thus, in some males erectile dysfunction may be due to anxiety or depression, with no apparent somatic or organic impairment. In other cases, erectile dysfunction is associated with atherosclerosis of the arteries supplying blood to the penis. In still other cases, the dysfunction may be due to venous leakage or abnormal drainage in which there is leakage from veins in the penis such that sufficient pressure for an erection can be neither obtained nor maintained. In still other cases, the dysfunction is associated with a neuropathy or due to nerve damage arising from, for example, surgery or a pelvic injury. Typically, multiple factors are responsible for impotence.

Pharmacological, biophysical and molecular studies have revealed multiple subtypes for membrane ion channels that form potassium selective pores in the plasma membrane of many mammalian cells. One can classify the family of K channels simply by their respective gating properties. In other words, a comparison of the pharmacological and electrophysiological properties of potassium channels has given rise to an operational definition for grouping the various subtypes based largely on their gating properties. At present, potassium channels of known amino acid sequence comprise two distantly related protein families. One of these channel families is termed, "voltage-gated," the other channel family is termed "inward rectifying."

The structure of the voltage-gated channel protein is known to be comprised of six membrane spanning domains in each subunit, each of which is regulated by changes in membrane potential. B. Hille, "Ionic Channels of Excitable Membranes" (Sinauer, Sunderland, Mass., 1992). Voltage-gated potassium channels sense changes in membrane potential and move potassium ions in response to this alteration in the cell membrane potential. Molecular cloning studies on potassium channel proteins has yielded information primarily for members of the voltage-gated family of potassium channels. Various genes encoding these voltage-gated family of potassium channel proteins have been cloned using Drosophila genes derived from both the Shaker, Shaw and Shab loci; Wei, A. et. al., Science (1990) Vol. 248 pp. 599–603.

Unlike the voltage-gated channel proteins with six membrane spanning regions, the inward rectifier channels have only two membrane spanning domains, each sensitive to changes in the net potassium concentration. Within this class of channels are the ATP-sensitive potassium channels. These channels are classified by their sensitivity to concentration fluxes in ATP. The ATP-sensitive, or ATP-gated, potassium channel is an important class of channels that links the bioenergetic situation of the cell to changes in cell function. These channels are blocked by high intracellular ATP concentrations and are open when ATP decreases. Lazdunski (1992); M. Lazdunski et al., "ATP-Sensitive K<+> Channels", Renal Physiol. Biochem. Vol. 17: pp. 118–120 (1994).

Although ATP-gated potassium channels were originally described in cardiac tissue, Noma, A. Nature (1983) Vol. 305 pp. 147–148, they have subsequently been described in pancreatic beta-cells, Cook et. al., Nature (1984) Vol. 311 pp. 271–273, vascular smooth muscle, Nelson, M. T. et. al., Am. J. Physiol. (1990) Vol. 259 pp. C3–C18 and in the thick ascending limb of the kidney, Wang, W. et. al. Am. J. Physiol. (1990) Vol. 258, pp. F244–F-253.

The ATP-sensitive or ATP-gated potassium channels play an important role in human physiology. The ATP-sensitive potassium channel, like other potassium channels, selectively regulate the cell's permeability to potassium ions. These channels function to regulate the contraction and relaxation of the smooth muscle by opening or closing the channels in response to the modulation of receptors or potentials on the cell membrane. When ATP-sensitive potassium channels are opened, the increased permeability of the cell membrane allows more potassium ions to migrate outwardly so that the membrane potential shifts toward more negative values. When the membrane potential shifts toward more negative values the opening of the voltage-dependent calcium channels is reduced, this reduces the influx of calcium ions into the cell because the calcium channels become "increasingly less open" as the membrane potential becomes more negative. Consequently, drugs having ATP-sensitive potassium channel opening activity, drugs known as potassium channel openers, can relax vascular smooth muscle and are useful as hypotensive and coronary vasodilating agents.

A relatively large number of compounds are now known which open cell membrane ATP-sensitive potassium channels, particularly in smooth muscle: minoxidil sulfate, diazoxide and nicorandil are well known potassium channel openers. The target site for these agents is presumably on the potassium channel itself, but may also be on an associated regulatory protein.

Potassium channel openers represent a widely diverse series of compounds which all have the reported effect of opening only a subset of channels described as sensitive to ATP. As explained above, these compounds cause physiological responses by increasing membrane permeability to potassium, this leads to hyperpolarization of the cell membrane and temporal desensitization to electrical and chemical stimuli.

Openers which target these channels have been synthesized as possible drugs in hypertension, angina pectoris, coronary heart disease, asthma, and urinary incontinence. There are various references which describe potassium channel openers:

Cook et al., "Potassium Channels: Structure, Classification, Function and TherapeuticPotential", ed. N. S. Cook, Ellis Horwood, Chichester (1990), p.p. 181–255;

David W. Robertson et al. , Journal of Medicinal Chemistry, "Potassium Channel Modulators: Scientific Applications and Therapeutic Promise," vol. 33, No. 6, June 1990, pp. 1529–1541;

Gillian Edwards et al., "Structure-Activity Relationships of K+Channel Openers," vol. 11, No. 10, October 1990, pp. 417–422;

Valerie A. Ashwood et al., "Synthesis and Antihypertensive Activity of Pyran Oxygen and Amide Nitrogen Replacement Anal oges of the Potassium Channel Activator Cromakalim," Journal of Medicinal Chemistry, vol. 34, No. 11, November 1991, pp. 3261–3267;

Susan D. Longman et al., "Potassium Channel Activator Drugs: Mechanism of Action, Pharmacological Properties, and Therapeutic Potential," Medicinal Research Reviews, vol. 12, No. 2, Mar. 1, 1992, pp. 73–148; and Karnail S. Atwal, "Modulation of Potassium Channels by Organic Molecules," Medicinal Research Reviews, vol. 12, No. 6, November 1992, pp. 569–591.

Agents which elevate cGMP levels are also well known and can work through any of several mechanisms. Agents which selectively inhibit an enzyme predominantly involved in cGMP breakdown, for example a cGMP phosphodiesterase (cGMP PDE), constitute one example. Other phosphodiesterases can also hydrolyze cGMP, and inhibitors of these enzymes including compounds such as rolipram, zaprinast and xanthine derivatives such as caffeine, theophylline and theobromine, can accordingly influence cGMP levels. Other compounds which increase cGMP levels can do so through different mechanisms including the activation of soluble guanylate cyclase or membrane-bound guanylate cyclase, either directly as in the case of atrial natriuretic peptide, or indirectly. Other compounds act to increase cellular cGMP levels by modulation of cytokines. Other classes of cGMP elevators include muscarinic agonists, which can elevate cGMP levels without altering phosphodiesterase activity. Some prostaglandins such as $PGE_1$ are also known cGMP elevators. Kanba et. al., J. Neurochem., Vol. 57, No. 6,1991.

Cyclic guanosine 3',5'-monophosphate phosphodiesterase (cGMP PDE) inhibitors are widely known as cardiovascular agents for the treatment of conditions such as angina, hypertension, and congestive heart failure. More recently cGMP PDE inhibitors have been found to be effective for the treatment of impotence, importantly by oral administration. See, for example, PCT/EP94/01580, published as WO 94/28902. It is believed that such compounds may manifest their therapeutic effects by achieving high cGMP levels through inhibiting phosphodiesterase, thereby relaxing and expanding cavernosal cells and blocking the outflow of blood from the penis.

SUMMARY OF THE INVENTION

This invention provides a method of treating impotence (also known in the art and referred to herein as "male erectile dysfunction"), especially in humans, comprising co-administering to a patient in need of such treatment an effective amount of:

(1) a compound selected from potassium channel openers (also referred to as potassium channel activators), and (2) a compound which elevates cGMP levels (herein also referred to as a cGMP elevator).

Reference to a compound or agent within the scope of (1) or (2), above, such as to a potassium channel opener and/or to a cGMP elevator, both in this disclosure and the appendant claims, shall at all times be understood to include all active forms of such agents, including the free form thereof (e.g., the free acid or base form) and also all pharmaceutically acceptable salts, prodrugs, polymorphs, hydrates, solvates, isomers, stereoisomers (e.g. diastereomers and enantiomers), tautomers, and so forth. Active metabolites of either the potassium channel openers or the cGMP elevator, in any form, are also included.

As the cGMP elevator, cGMP PDE inhibitors are preferred. cGMP PDE inhibitors which are selective for cGMP PDEs rather than cyclic adenosine 3',5'-monophosphate phosphodiesterases (cAMP PDEs) and/or which are selective inhibitors of the cGMP $PDE_v$ isoenzyme are particularly preferred. Such particularly preferred cGMP PDE inhibitors are disclosed in U.S. Pat. Nos. 5,250,534, 5,346,901, 5,272, 147, and in the international patent application published as WO 94/28902 designating, inter alia, the U.S., each of which is incorporated herein by reference.

Preferred combinations of a potassium channel opener and a cGMP PDE elevator useful herein are "synergistic", meaning that the therapeutic effect of co-administering compounds selected from (1) and (2) as defined above is greater than additive. Thus, co-administering both therapeutic agents produces an effect which is greater than the sum of the effects of each agent administered alone. Such synergy is advantageous in that it allows for each therapeutic agent typically to be administered in an amount less than if the combined therapeutic effects were additive. Thus, therapy can be effected for patients who, for example, do not respond adequately to the use of one component at what would be considered a maximal strength dose. Additionally, by administering the components in lower amounts relative to the case where the combined effects are additive, side effects such as any priapism or pain at the site of injection can be minimized or avoided in many cases. Such synergy can be demonstrated by the tests disclosed below.

The synergy of such preferred combinations is provided as a further feature of the invention, and accordingly the invention provides a method for achieving a synergistic therapeutically effective level of impotence treatment, comprising co-administering to a mammal in need of such treatment (1) an amount of a first compound selected from potassium channel openers; and (2) an amount of a second compound selected from compounds which elevate cGMP levels;

wherein the amount of the first compound alone and the amount of the second compound alone are each insufficient to achieve the synergistic therapeutically effective level of impotence treatment, but wherein the combined effect of the amounts of the first and second compounds is greater than the sum of the levels of therapeutic effects of impotence treatment achievable with the individual amounts of the first and second compound.

Additional preferred combinations include those which can be taken "on demand", as opposed to needing to be taken chronically. Such preferred combinations include those which modulate the sexual response such that the patient responds to sexual (e.g., visual) stimulation, as opposed to compositions which act by causing an erection in the absence of sexual stimulation.

Additional preferred combinations include those which are "fast acting", meaning that the time from administration to the point at which the sexual response can be modulated is less than about two hours, preferably less than about one hour, more preferably on the order of a half hour or less, and even more preferably within 10 to 15 minutes.

"Co-administration" when used in this disclosure and the appendant claims, for example in referring to a combination of a potassium channel openers and a cGMP PDE inhibitor, means that the individual components can be administered together as a composition if the route of administration for each component is the same. Thus the invention further provides a composition comprising (1) a first compound, said first compound being selected from potassium channel openers;
(2) a second compound which elevates cGMP levels; and
(3) a pharmaceutically acceptable vehicle, diluent or carrier. A preferred group of compositions are synergistic. Such synergistic compositions, which are provided as a further feature of the invention, comprise
(1) an amount of a first compound selected from potassium channel openers;
(2) an amount of a second compound selected from compounds which elevate cGMP levels;

wherein the amount of the first compound alone and the amount of the second compound alone are each insufficient to achieve a synergistic therapeutically effective level of impotence treatment, but wherein the effect of a composition comprising said amounts of said first and second compounds is greater than the sum of the levels of therapeutic effects of impotence treatment achievable with the individual amounts of said first and second compound; and a pharmaceutically acceptable vehicle, diluent or carrier.

"Co-administration" also includes administering each of compounds (1) and (2) separately but as part of the same therapeutic treatment program or regimen, and it is contemplated that separate administration of each compound, at different times and by different routes, will sometimes be recommended. Thus, the two compounds need not necessarily be administered at essentially the same time or in any order. In a preferred embodiment, administration is timed so that the peak pharmacokinetic effect of one compound coincides with the peak pharmacokinetic effect for the other. If co-administered separately, it is also preferred that both of compounds (1) and (2) be administered in an oral dosage form.

Reference herein to a "combination" is to the co-administration of a compound selected from (1) and a compound selected from (2), each as defined above, either as a composition or separately, e.g., by different routes of administration.

The compositions of this invention are also useful for the treatment of sexual dysfunction in female mammals, including humans. Thus the compositions are useful, for example, in the treatment of female sexual dysfunction including orgasmic dysfunction related to clitoral disturbances. As in the case of male mammals, compositions which are synergistic, which can be taken on demand, and which modulate the female sexual response are preferred. Preferred compounds, compositions, and combinations (e.g. of compounds for separate administration) for the treatment of female sexual dysfunction are the same as those disclosed herein for the treatment of male erectile dysfunction.

Methods for the treatment of female sexual dysfunction are analogous to those presented herein for the treatment of impotence or erectile dysfunction in male animals.

Since the present invention has an aspect that relates to the treatment of impotence or of female sexual dysfunction by treatment with a combination of compounds which may be co-administered separately, the invention also relates to combining separate pharmaceutical compositions in kit form. The kit comprises two separate pharmaceutical compositions: (1) a composition comprising a compound selected from potassium channel openers, and a pharmaceutically acceptable vehicle, diluent or carrier; and (2) a composition comprising a compound selected from agents which elevate cGMP levels, and a pharmaceutically acceptable vehicle, diluent or carrier and a container. The amounts of (1) and (2) are such that, when co-administered separately, the impotence condition or condition of female sexual dysfunction is treated and/or remediated. The kit comprises a means for containing the separate compositions such as a container, divided bottle or a divided foil packet, wherein each compartment contains a plurality of dosage forms (e.g., tablets) comprising (1) or (2). Alternatively, rather than separating the active ingredient-containing dosage forms, the kit may contain separate compartments each of which contains a whole dosage which in turn comprises separate dosage forms. An example of this type of kit is a blister pack wherein each individual blister contains two (or more) tablets, one (or more) tablet(s) comprising pharmaceutical composition (1), and the second one (or more) tablet(s) comprising pharmaceutical composition (2). Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician. In the case of the instant invention a kit therefore comprises a therapeutically effective amount of (1) a composition comprising a compound selected from potassium channel openers, and a pharmaceutically acceptable vehicle, diluent or carrier, in a first dosage form;
(2) a composition comprising a compound selected from compounds which elevate cGMP levels, and a pharmaceutically acceptable vehicle, diluent or carrier, in a second dosage form; and
(3) a container for containing said first and second dosage forms.

An example of such a kit, alluded to above, is a so-called blister pack. Blister packs are well known in the packaging industry and are widely used for the packaging of pharmaceutical unit dosage forms such as tablets, capsules, and the like. Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. Tablet(s) or capsule(s) can then be removed via said opening.

It may be desirable to provide a memory aid on the kit, e.g., in the form of numbers next to the tablets or capsules whereby the numbers correspond with the days of the regimen during which the tablets or capsules so specified should be ingested. Another example of such a memory aid is a calendar printed on the card, e.g., as follows "First Week, Monday, Tuesday, . . . etc . . . Second Week, Monday, Tuesday, . . . ", etc. Other variations of memory aids will be readily apparent. A "daily dose" can be a single tablet or capsule or several pills or capsules to be taken on a given day. Also, a daily dose of the first compound can consist of one tablet or capsule while a daily dose of the second compound can consist of several tablets or capsules and vice versa. The memory aid should reflect this.

Other pharmaceutical components may also be optionally included as part of the combinations useful in this invention so long as they do not interfere or adversely affect the effects of the potassium channel opener/cGMP elevator combination.

Preferred combinations further include (1) a cGMP PDE inhibitor and any suitably potent potassium channel opener such as nicorandil; and (2) a cGMP PDE inhibitor that is selective for the $PDE_V$ isoenzyme. Compounds selective for the $PDE_V$ isoenzyme are disclosed, for example, in PCT/EP94/01580, published as WO 94/28902 and which designates, inter alia, the United States, and which is incorporated herein by reference.

Preferred cGMP PDE inhibitors include sildenafil which has the structure:

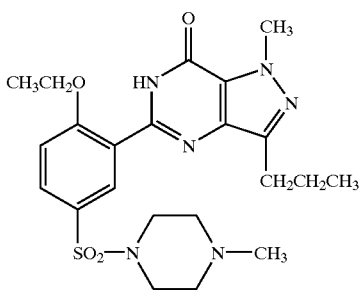

and pharmaceutically acceptable salts thereof, and the compound having the structure:

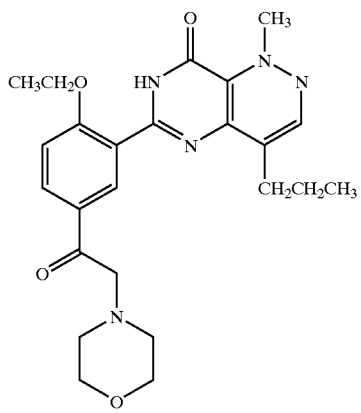

and pharmaceutically acceptable salts thereof. The second compound is disclosed, for example, in U.S. Pat. Nos. 5,272,147 and 5,426,107, both incorporated herein by reference.

Other preferred cGMP PDE inhibitors include 3-ethyl-5-[2-(2-methoxyethoxy)-5-(4-methylpiperazin-1-ylsulphonyl) pyridin-3-yl]-2-(pyridin-2-yl)methyl-2,6-dihydro-7H-pyrazolo[4,3-d]pyrimidin-7-one; 3-ethyl-5-[5-(4-ethylpiperazin-1-ylsulphonyl)-2)2-methoxyethoxy)pyridin-3-yl]-2-(pyridin-2-yl)methyl-2,6-dihydro-7H-pyrazolo[4,3-d]pyrimidin-7-one; 3-ethyl-5-[5-(4-ethyl-4-oxidopiperazin-1-ylsulphonyl)-2-(2-methoxyethoxy)pyridin-3-yl]2-(pyridin-2-yl)methyl-2,6-dihydro-7H-pyrazolo[4,3-d] pyrimidin-7-one; 5-[2-(2-methoxyethyoxy)-5-(4-methylpiperazin-1-ylsulphonyl)pyridin-3-yl]-3-n-propyl-2-(pyridin-2-yl)methyl-2,6-dihydro-7H-pyrazolo[4,3-d]pyrimidin-7-one; 5-[5-(4-ethylpiperazin-1-ylsulphonyl)-2-(2-methoxyethoxy)pyridin-3-yl]-3-n-propyl-2-(pyridin-2-yl)methyl-2,6-dihydro-7H-pyrazolo[4,3-d]pyrimidin-7-one; (+)-3-ethyl-5-[5-(4-ethylpiperazin-1-ylsulphonyl)-2-(2-methoxy-1(R)-methylethoxy)pyridin-3-yl]-2-methyl-2,6-dihydro-7-Hpyrazolo[4,3-d]pyrimidin-7-one; 3-ethyl-5-[5-(4-ethylpiperazin-1-ylsulphonyl)-2-(2-methoxy-1(R)-methylethoxy)pyridin-3-yl]-2-(6-methylpyridin-2-yl) methyl-2,6-dihydro-7H-pyrazolo[4,3-d]pyrimidin-7-one; 5-[2-ethoxy-5-(4-ethylpiperazin-1-ylsulphonyl)pyridin-3-yl]-3-ethyl-2-(6-methoxypyridin-2-yl)methyl-2,6-dihydro-7H-pyrazolo[4,3-d]pyrimidin-7-one; 5-[2-i-butoxy-5-(4-ethylpiperazin-1-ylsulphonyl)pyridin-3-yl]-2,3-diethyl-2,6-dihydro-7H-pyrazolo[[4,3-d]pyrimidin-7-one; 5-[2-ethoxy-5-(4-ethylpiperazin-1-ylsulphonyl)pyridin-3-yl]-3-ethyl-2-[1-pyridin-2-yl)ethyl]2,6-dihydro-7H-pyrazolo[4,3-d] pyrimidin-7-one or the pharmaceutically acceptable salts thereof A preferred pharmaceutically acceptable salt of sildenafil for use in this invention is the citrate salt.

Also preferred are compounds disclosed in PCT/EP95/00183, published as WO 95/19978 designating, inter alia, the United States, and herein incorporated by reference, said compounds having the formula

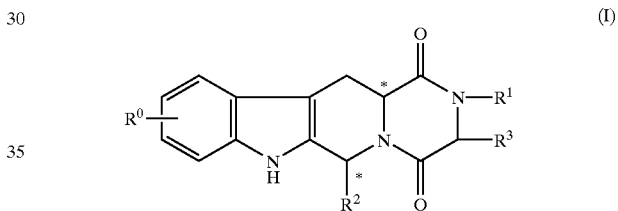

(I)

and salts and solvates thereof, in which:

$R^0$ represents hydrogen, halogen or $C_{1-6}$alkyl,;

$R^1$ represents hydrogen, $C_{1-6}$alkyl, $C_{2-6}$alkenyl, $C_{2-6}$alkynyl, halo$C_{1-6}$alkyl, $C_{3-8}$cycloalkyl, $C_{3-8}$cycloalkyl$C_{1-3}$alkyl, aryl$C_{1-3}$alkyl or heteroaryl$C_{1-3}$alkyl;

$R^2$ represents an optionally substituted monocyclic aromatic ring selected from benzene, thiophene, furan and pyridine or an optionally substituted bicyclic ring

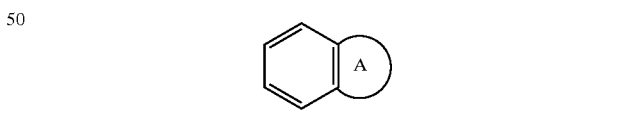

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and $R^3$ represents hydrogen or $C_{1-3}$alkyl, or $R^1$ and $R^3$ together represent a 3- or 4-membered alkyl or alkenyl chain.

A preferred subset of compounds having formula Ia (also disclosed in WO 95/19978) includes compounds of the formula

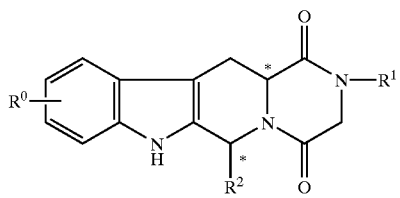

(Ia)

and salts and solvates thereof, in which:
$R^0$ represents hydrogen, halogen or $C_{1-6}$alkyl;
$R^1$ represents hydrogen, $C_{1-6}$alkyl, halo$C_{1-6}$alkyl, $C_{3-8}$cycloalkyl, $C_{3-8}$cycloalkyl-$C_{1-3}$alkyl, aryl$C_{1-3}$alkyl or heteroaryl$C_{1-3}$alkyl; and
$R^2$ represents an optionally substituted monocyclic aromatic ring selected from benzene thiophene, furan and pyridine or an optionally substituted bicyclic ring

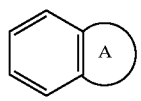

attached to the rest of the molecule via one of the benene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen.

A specific compound within formula (I) is:
(6R, 12aR)-2,3,6,7,12,12a-hexahydro-2-methyl-6-(3,4-methylenedioxyphenyl)-pyrazino[2',1'6,1]pyrido[3,4-b]indole-1,4-dione.

Preferred potassium channel openers include nicorandil, diazoxide, cromakalim, levcromakalim, pinacidil, lemakalim and minoxidil and also pharmaceutically acceptable salts or isomers thereof. Especially preferred potassium channel openers include nicorandil, diazoxide and minoxidil. Preferred specific combinations include any of these in combination with sildenafil or a pharmaceutically acceptable salt thereof, particularly the citrate salt. Most preferred are sildenafil citrate in combination with nicorandil. A variety of potassium channel openers are described in U.S. Pat. Nos. 5,464,867; 5,466,712; 5,403,853; 5,403,854; 5,397,790; 5,401,753; 5,872,139; and 5,905,156, the teachings of which are incorporated herein by reference.

Specific combinations of a potassium channel opener and a cGMP elevator useful in this invention include any potassium channel opener in combination with sildenafil. Combinations of sildenafil, especially sildenafil citrate, with a potassium channel opener, including any of those previously noted, are preferred.

DETAILED DESCRIPTION

The cGMP PDE inhibitors useful in this invention as cGMP elevators may be widely chosen from among any of those already known to the art or subsequently discovered and/or hereafter developed. Suitable cGMP PDE inhibitors include those disclosed in any of the following U.S. patents, all of which are incorporated herein by reference:

a 5-substituted pyrazolo[4,3-d]pyrimidine-7-one as disclosed in U.S. Pat. No. 4,666,908;

a griseolic acid derivative as disclosed in any of U.S. Pat. Nos. 4,634,706, 4,783,532, 5,498,819, 5,532,369, 5,556,975, and 5,616,600;

a 2-phenylpurinone derivative as disclosed in U.S. Pat. No. 4,885,301;

a phenylpyridone derivative as disclosed in U.S. Pat. No. 5,254,571;

a fused pyrimidine derivative as disclosed in U.S. Pat. No. 5,047,404;

a condensed pyrimidine derivative as disclosed in U.S. Pat. No. 5,075,310;

a pyrimidopyrimidine derivative as disclosed in U.S. Pat. No. 5,162,316;

a purine compound as disclosed in U.S. Pat. No. 5,073,559;

a quinazoline derivative as disclosed in U.S. Pat. No. 5,147,875;

a phenylpyrimidone derivative as disclosed in U.S. Pat. No. 5,118,686;

an imidazoquinoxalinone derivative or its aza analog as disclosed in U.S. Pat. Nos. 5,055,465 and 5,166,344;

a phenylpyrimidone derivative as disclosed in U.S. Pat. No. 5,290,933;

a 4-aminoquinazoline derivative as disclosed in U.S. Pat. No. 5,436,233 or 5,439,895;

a 4,5-dihydro-4-oxo-pyrrolo[1,2-a]quinoxaline derivative as disclosed in U.S. Pat. No. 5,405,847;

a polycyclic guanine derivative as disclosed in U.S. Pat. No. 5,393,755;

a nitogenous heterocyclic compound as disclosed in U.S. Pat. No. 5,576,322;

a quinazoline derivative as disclosed in U.S. Pat. No. 4,060,615; and a 6-heterocyclyl pyrazolo[3,4-d]pyrimidin4-one as disclosed in U.S. Pat. No. 5,294,612.

Other disclosures of cGMP PDE inhibitors include the following, all of which are herein incorporated by reference:

European patent Application (EPA) publication no. 0428268;

European patent 0442204;

International patent application publication no. WO 94/19351;

Japanese patent application 5-222000;

European Journal Of Pharmacology, 251, (1994), 1; and

International patent application publication no. WO 94/22855.

The potassium channel opening activity of a compound, and therefore its suitability for use in the present invention, can be determined using a number of conventional assays in vitro. Potassium channel openers exhibit potassium channel opening activity in relation to the plasma lemma membrane as demonstrated by their influence at concentrations in the region of 1 to 500 nM on various smooth muscle preparations in accordance with or analogous to the methods described in Quast, Brit. J. Pharmac., 91, 569–578 (1987).

The cGMP PDE inhibition of a compound can also be determined by standard assays known to the art, for example as disclosed in U.S. Pat. No. 5,250,534, incorporated herein by reference. Compounds which are selective inhibitors of cGMP PDE relative to cAMP PDE are preferred, and determination of such compounds is also taught in U.S. Pat. No. 5,250,534. Particularly preferred are compounds which selectively inhibit the $PDE_v$ isoenzyme, as disclosed in the aforementioned PCT/EP94/01580, published as WO 94/28902.

As disclosed above, individual compounds of the combinations useful in this invention will generally be administered separately, each by its own customary and known route, and in certain cases the routes of administration may be different. In a preferred embodiment, administration will generally be timed so that both the potassium channel opener and the cGMP elevator both coincide, or nearly coincide, in reaching their maximum pharmacokinetic effect. The routes of administration can be any of those known to the art such as oral, parenteral via local injection intracavernosally or intraurethrally, or transdermal as by applying the active component in a gel or other such formulation topically to the penis. Each component can be formulated as known in the art, usually together with a pharmaceutically acceptable vehicle, diluent or carrier, for example as a tablet, capsule, lozenge, troche, elixir, solution, or suspension for oral administration, in a suitable injectable vehicle for parenteral administration, or as a lotion, ointment or cream for topical application. In a preferred embodiment, the cGMP elevator and the potassium channel opener are each co-administered orally, together or separately.

The exact dose of each component administered will, of course, differ depending on the specific components prescribed, on the subject being treated, on the severity of the impotence or of the female sexual dysfunction, on the manner of administration and on the judgment of the prescribing physician. Thus, because of patient-to-patient variability, the dosages given below are a guideline and the physician may adjust doses of the compounds to achieve the treatment that the physician considers appropriate for the patient, male or female. In considering the degree of treatment desired, the physician must balance a variety of factors such as he age of the patient and the presence of other diseases or conditions (e.g., ardiovascular disease). In general, the cGMP elevator will be administered in a range of from 0.5 to 200 mg per day, preferably 5 to 125 mg per day, more preferably 25–100 mg per day. The potassium channel opener will generally be administered in an amount of from 0.01 mg to 50 mg per day, preferably from 0.5 to 10 mg per day. If the cGMP PDE elevator is a prostaglandin, it is generally administered intracavemosally by injection in an amount of from 1 ng to 100 $\mu$g or intraurethrally in an amount of 100 $\mu$g to 2 mg per day. Generally, the injected amount is in a volume which usually will not exceed 1 ml. The carrier or diluent is typically sterile physiological saline or another physiologically acceptable salt solution. Oral administration of prostaglandins is also feasible. Japanese Journal of Urology, 83(10):1655–1661, (1992).

As previously disclosed, the combination of cGMP PDE elevator and potassium channel opener can be administered as a composition. Thus, the compounds of this invention can be administered together in any conventional oral, parenteral, rectal or transdermal dosage form, usually also together with a pharmaceutically acceptable vehicle, diluent or carrier.

For oral administration, a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 15th Edition (1975).

A combination of a potassium channel opener and a cGMP elevator such as a cGMP PDE inhibitor can be tested in vivo in either a beagle dog or monkey model. The following description is with respect to monkeys, but those skilled in the art will easily recognize that the test applies equally and can be adapted to beagle dogs.

Mature adult male monkeys, typically either *Cercopithecus aethiops* (green monkey) or *Macaca fasciculata* (cynomologous) having a weight range of 4 to 8 kg are used. Animals are anesthetized with diazepam (2.5 mg), ketamine chloride (20 $\mu$g/kg i.m. supplemented as appropriate) and given the test compound(s) dissolved in saline intracavernosally (0.3 ml). Animals are placed supine, the penis stretched out, and a rubber band placed around the root of the base as a tourniquet kept in place for three minutes after the injection. The solution is injected through a 27G needle into one of the corpus cavernosa and 5, 10, 25, 30, 60, and 180 minutes later tumescence (increase in volume) and rigidity of the penis is estimated visually and by palpitation. To determine the threshold effect using the injectable solution, a series of animals are used covering an appropriate dose range for the test compound or compounds.

The combination of a potassium channel opener and cGMP elevator can also be tested clinically, typically orally, in humans as well as in an animal model. Each compound is administered singly at different times to a population of male patients, each compound being administered in an amount which produces little or no response, typically less than a 50% response, as measured by the Rigiscan Clinical Evaluation parameters (see Kaneko et al., J. Urol. 136, 1026–1029 (1986); and Ogric et al., J. Urol., 154, 1356–1359 (1995) ) of rigidity and tumescence, in conjunction with the International Index of Erectile Function (IIEF) questionnaire which evaluates patient and partner satisfaction. By administering each compound singly, it is meant that one compound is administered, followed at a later time by the second compound after having allowed an appropriate time for washout of the first compound. After the washout period for each compound administered singly, the compound are co-administered in a manner such that both compounds co-operate pharmacokinetically, preferably such that the peak pharmacokinetic effect due to each coincides. Co-administration is evaluated according to the regiscan parameters mentioned above and by IIEF questionnaires, thereby providing a basis for comparison of the effects of co-administration with that for each single administration and to demonstrate a synergistic effect.

The compounds and combinations of this invention generally will be administered in a convenient formulation. The following formulation examples are illustrative only and are not intended to limit the scope of the present invention.

In the formulations which follow, "active ingredient" means a compound(s) of this invention.

Formulation 1: Gelatin Capsules

Hard gelatin capsules are prepared using the following:

| Ingredient | Quantity (mg/capsule) |
| --- | --- |
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
| --- | --- |
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

What is claimed is:

1. A method of treating impotence comprising co-administering to a patient in need of such treatment an effective amount of:

(1) a potassium channel opener selected from the group consisting of nicorandil, cromokalim, levcromakalim, lemakalim, pinacidil, diazoxide and minoxidil or a pharmaceutically acceptable salt thereof, and (2) a compound which elevates cGMP levels;

wherein (1) and (2) are each administered orally.

2. A method as defined in claim 1 wherein said cGMP elevator is a cGMP PDE inhibitor.

3. A method as defined in claim 1 wherein said cGMP PDE elevator is a prostaglandin.

4. A method as defined in claim 2 wherein said cGMP PDE inhibitor is selective for the cGMP $PDE_v$ isoenzyme.

5. A method as defined in claim 4 wherein said cGMP PDE inhibitor is sildenafil or a pharmaceutically acceptable salt thereof.

6. A method as defined in claim 5 wherein said salt is the citrate salt.

7. A method as defined in claim 2 wherein said cGMP PDE inhibitor has the structure

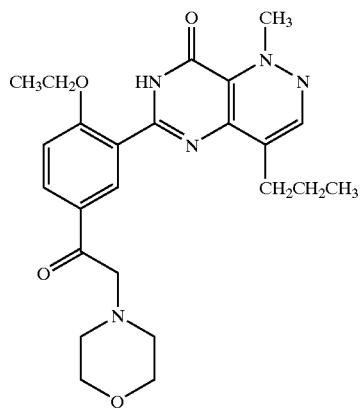

8. A method as defined in claim 2 wherein said cGMP PDE inhibitor is 3-ethyl-5-[2-(2-methoxyethoxy)-5-(4-methylpiperazin-1-ylsulphonyl)pyridin-3-yl]-2-(pyridin-2-yl)methyl-2,6-dihydro-7H-pyrazolo[4,3-d]pyrimidin-7-one; 3-ethyl-5-[5-(4-ethylpiperazin-1-ylsulphonyl)-2)2-methoxyethoxy)pyridin-3-yl]-2-(pyridin-2-yl)methyl-2,6-dihydro-7H-pyrazolo[4,3-d]pyrimidin-7-one; 3-ethyl-5-[5-(4-ethyl-4-oxidopiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one; 5-[2-(2-methoxyethyoxy)-5-(4-methylpiperazin-1-ylsulphonyl) pyridin-3-yl]-3-n-propyl-2-(pyridin-2-yl)methyl-2,6-dihydro-7H-pyrazolo[4,3-d]pyrimidin-7-one; 5-[5-(4-ethylpiperazin-1-ylsulphonyl)-2-(2-methoxyethoxy) pyridin-3-yl]-3-n-propyl-2-(pyridin-2-yl)methyl-2,6-dihydro-7H-pyrazolo[4,3-d]pyrimidin-7-one; (+)-3-ethyl-5-[5-(4-ethylpiperazin-1-ylsulphonyl)-2-(2-methoxy-1(R)-methylethoxy)pyridin-3-yl]-2-methyl-2,6-dihydro-7-Hpyrazolo[4,3-d]pyrimidin-7-one; 3-ethyl-5-[5-(4-ethylpiperazin-1-ylsulphonyl)-2-(2-methoxy-1(R)-methylethoxy)pyridin-3-yl]-2-(6-methylpyridin-2-yl) methyl-2,6-dihydro-7H-pyrazolo[4,3-d]pyrimidin-7-one; 5-[2-ethoxy-5-(4-ethylpiperazin-1-ylsulphonyl)pyridin-3-yl]-3-ethyl-2-(6-methoxypyridin-2-yl)methyl-2,6-dihydro-7H-pyrazolo[4,3-d]pyrimidin-7-one; 5-[2-i-butoxy-5-(4-ethylpiperazin-1-ylsulphonyl)pyridin-3-yl]-2,3-diethyl-2,6-dihydro-7H-pyrazolo[[4,3-d]pyrimidin-7-one; 5-[2-ethoxy-5-(4-ethylpiperazin-1-ylsulphonyl)pyridin-3-yl]-3-ethyl-2-[1-pyridin-2-yl)ethyl]2,6-dihydro-7H-pyrazolo[4,3-d] pyrimidin-7-one or the pharmaceutically acceptable salts of said compounds.

9. A method as defined in claim 1 wherein said potassium channel opener is nicorandil or a pharmaceutically acceptable salt thereof.

10. A method as defined in claim 1 wherein said first compound is nicorandil or a pharmaceutically acceptable salt thereof and said second compound is sildenafil or a pharmaceutically acceptable salt thereof.

11. A method as defined in claim 10 wherein said first compound is nicorandil and said second compound is sidenafil citrate.

12. A method as defined in claim 1 wherein (1) and (2) are administered together in a composition.

13. A method as defined in claim 1 wherein (1) and (2) are administered separately.

14. A method for achieving a synergistic therapeutically effective level of impotence treatment, comprising co-administering orally to a mammal in need of such treatment
(1) an amount of a potassium channel opener selected from the group consisting of nicorandil, cromokalim, levcromakalim, lemakalim, pinacidil, diazoxide and minoxidil or a pharmaceutically acceptable salt thereof; and
(2) an amount of a second compound selected from compounds which elevate cGMP levels;
wherein the amount of the potassium channel opener alone and the amount of the second compound alone is insufficient to achieve the synergistic therapeutically effective level of impotence treatment, but wherein the combined effect of the amounts of the potassium channel opener and the second compound is greater than the sum of the levels of therapeutic effects of impotence treatment achievable with the individual amounts of the potassium channel opener and the second compound.

15. A method as defined in claim 14 wherein said cGMP elevator is a cGMP PDE inhibitor.

16. A method as defined in claim 15 wherein said cGMP elevator is a prostaglandin.

17. A method as defined in claim 15 wherein said cGMP PDE inhibitor is selective for the cGMP $PDE_V$ isoenzyme.

18. A method as defined in claim 17 wherein said cGMP PDE inhibitor is sildenafil or a pharmaceutically acceptable salt thereof.

19. A method as defined in claim 18 wherein said salt is the citrate.

20. A method as defined in claim 15, wherein said cGMP PDE inhibitor has the structure

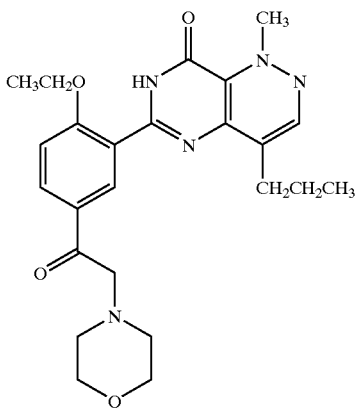

or is a pharmaceutically acceptable salt thereof.

21. A method as defined in claim 15 wherein said wherein said cGMP PDE inhibitor is 3-ethyl-5-[2-(2-methoxyethoxy)-5-(4-methylpiperazin-1-ylsulphonyl)pyridin-3-yl]-2-(pyridin-2-yl)methyl-2,6-dihydro-7H-pyrazolo[4,3-d]pyrimidin-7-one; 3-ethyl-5-[5-(4-ethylpiperazin-1-ylsulphonyl)-2)2-methoxyethoxy)pyridin-3-yl]-2-(pyridin-2-yl)methyl-2,6-dihydro-7H-pyrazolo[4,3-d]pyrimidin-7-one; 3-ethyl-5-[5-(4-ethyl-4-oxidopiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one; 5-[2-(2-methoxyethyoxy)-5-(4-methylpiperazin-1-ylsulphonyl)pyridin-3-yl]-3-n-propyl-2-(pyridin-2-yl)methyl-2,6-dihydro-7H-pyrazolo[4,3-d]pyrimidin-7-one; 5-[5-(4-ethylpiperazin-1-ylsulphonyl)-2-(2-methoxyethoxy)pyridin-3-yl]-3-n-propyl-2-(pyridin-2-yl)methyl-2,6-dihydro-7H-pyrazolo[4,3-d]pyrimidin-7-one; (+)-3-ethyl-5-[5-(4-ethylpiperazin-1-ylsulphonyl)-2-(2-methoxy-1(R)-methylethoxy)pyridin-3-yl]-2-methyl-2,6-dihydro-7-Hpyrazolo[4,3-d]pyrimidin-7-one; 3-ethyl-5-[5-(4-ethylpiperazin-1-ylsulphonyl)-2-(2-methoxy-1(R)-methylethoxy)pyridin-3-yl]-2-(6-methylpyridin-2-yl)methyl-2,6-dihydro-7H-pyrazolo[4,3-d]pyrimidin-7-one; 5-[2-ethoxy-5-(4-ethylpiperazin-1-ylsulphonyl)pyridin-3-yl]-3-ethyl-2-(6-methoxypyridin-2-yl)methyl-2,6-dihydro-7H-pyrazolo[4,3-d]pyrimidin-7-one; 5-[2-i-butoxy-5-(4-ethylpiperazin-1-ylsulphonyl)pyridin-3-yl]-2,3-diethyl-2,6-dihydro-7H-pyrazolo[[4,3-d]pyrimidin-7-one; or 5-[2-ethoxy-5-(4-ethylpiperazin-1-ylsulphonyl)pyridin-3-yl]-3-ethyl-2-[1-pyridin-2-yl)ethyl]2,6-dihydro-7H-pyrazolo[4,3-d]pyrimidin-7-one or the pharmaceutically acceptable salts of said compounds.

22. A method as defined in claim 14 wherein said potassium channel opener is nicorandil or a pharmaceutically acceptable salt thereof.

23. A method as defined in claim 14 which comprises (1) nicorandil; and (2) sildenafil or a pharmaceutically acceptable salt thereof.

24. A method as defined in claim 14 wherein said potassium channel opener (1) is nicorandil or a pharmaceutically acceptable salt thereof and (2) is sidenafil citrate.

25. A method for achieving a synergistic therapeutically effective level of treatment of female sexual dysfunction, comprising co-administering orally to a mammal in need of such treatment
(1) an amount of a first compound selected from potassium channel openers; and
(2) an amount of a second compound selected from compounds which elevate cGMP levels;
wherein the amount of the first compound alone and the amount of the second compound alone is insufficient to achieve the synergistic therapeutically effective level of treatment of female sexual dysfunction, but wherein the combined effect of the amounts of the first and second compounds is greater than the sum of the levels of therapeutic effects of female sexual dysfunction treatment achievable with the individual amounts of the first and second compound said first potassium channel opener compound is selected from the group consisting of nicorandil, cromokalim, leucromakalim, lemakalim, pinacidil, diazoxide, and minoxidil, or pharmaceutically acceptable salts thereof.

* * * * *